United States Patent [19]
Katsuda et al.

[11] Patent Number: 6,074,656
[45] Date of Patent: Jun. 13, 2000

[54] LONG-ACTING INSECTICIDAL MAT AND HEAT-TRANSPIRATION INSECTICIDAL METHOD USING THE SAME

[75] Inventors: Yoshio Katsuda, Nishinomiya; Koji Nakayama, Toyanaka; Tomoko Takahashi, Nishinomiya, all of Japan

[73] Assignee: Dainihon Jochugiku Co., Ltd., Osaka, Japan

[21] Appl. No.: 08/966,365

[22] Filed: Nov. 7, 1997

[30] Foreign Application Priority Data

Nov. 12, 1996 [JP] Japan ................................. 8-337433

[51] Int. Cl.$^7$ ...................................... A01N 25/08
[52] U.S. Cl. ........................... 424/411; 424/405; 424/409
[58] Field of Search ................... D23/330–336, D23/341; 424/405, 406, 409, 411

[56] References Cited

U.S. PATENT DOCUMENTS

| D. 92,948 | 8/1934 | Crowley | D23/336 |
|---|---|---|---|
| D. 93,181 | 8/1934 | Payne | D23/336 |
| 4,515,768 | 5/1985 | Hennart et al. | 424/40 |

FOREIGN PATENT DOCUMENTS

| 0596317 | 5/1994 | European Pat. Off. . |
|---|---|---|
| 0002331 | 1/1979 | Japan . |
| 0041201 | 10/1980 | Japan . |
| 5-194103 | 8/1993 | Japan . |
| 6-192007 | 7/1994 | Japan . |
| WO 96/03880 | 2/1996 | WIPO . |

OTHER PUBLICATIONS

Abstract. CA 124: 335676 Ito Wo9604786 Feb. 1996 Insect Pest Control.

*Primary Examiner*—Neil S. Levy
*Attorney, Agent, or Firm*—Oliff & Berridge, PLC

[57] ABSTRACT

The present invention provides a long-acting insecticidal mat which is applied to the electric mosquito-repellent mat system and is capable of maintaining the insecticidal effect for a long period, not less than five days, and a heat-transpiration insecticidal method using the mat, wherein a fibrous mat which is impregnated with not less than 50 mg per mat of an insecticidal ingredient of pyrethroid having not less than $4.0 \times 10^{-6}$ mmHg of vapor pressure at 20° C. is used by means of setting the mat on a radiation plate which has an area of 0.2 to 0.6 time as large as the base area of the mat and has a heating temperature of 70 to 170° C.

3 Claims, No Drawings

LONG-ACTING INSECTICIDAL MAT AND HEAT-TRANSPIRATION INSECTICIDAL METHOD USING THE SAME

FIELD OF THE INVENTION

The present invention relates to a fibrous mat containing an insecticidal ingredient, and to a heat-transpiration insecticidal method in which the mat is set on a radiation plate of a heating element to thereby transpire the insecticidal ingredient.

DESCRIPTION OF THE RELATED ART

Hitherto, as a method of heat-transpiring an insecticidal ingredient for killing insects or the like, (1) a mosquito-repellent incense and (2) an electric mosquito-repellent mat have been used favorably so far, and (3) a liquid mosquito-repellent, that is, a method of heat-transpiring an insecticidal solution by soaking an absorbent wick in the insecticidal solution and heating the upper part of the wick has been popular in recent years.

Of those, the electric mosquito-repellent mat works by means of setting a fibrous mat impregnated with an insecticidal ingredient on a radiation plate of the heat-transpiration apparatus having an approximately same shape as that of the mat, and heating the mat with electricity to transpire the insecticidal ingredient contained therein. The temperature in the middle of the radiation plate is set in the range of 140 to 180° C. The electric mosquito-repellent mat is a product which can be used with ease. However, since the whole base of the mat is heated by the radiation plate, even if a volatilization controlling agent is added thereto, the volatilizing amount of the insecticidal ingredient decreases with the time elapsed. For that reason, the mat is normally designed so as to be changed every day. Therefore, it only contains the insecticidal ingredient of pyrethroid in the amount to be used in a day, and it has been considered to be difficult to develop a long-acting insecticidal mat because of the properties of the product.

On the other hand, also in the liquid mosquito-repellent, the same insecticidal ingredient of pyrethroid as in the electric mosquito-repellent mat is used. However, the temperature of the heating element of the liquid mosquito-repellent is a little lower compared with that of the electric mosquito-repellent mat, since the structure is designed such that the upper part of the wick is indirectly heated. This system is so convenient that the effect of insecticidal ingredient may be kept for 30 to 60 days once a bottle of the insecticidal solution is set, whereas the fear of leakage of the solution etc. is unavoidable.

Attempt is made to develop a product into which the advantage of the electric mosquito-repellent mat system of easy handling is taken, and which maintains the effect for a long period. For example, Japan Patent Application Laid-open Nos. Hei 5-194103 and Hei 6-192007 disclose an insecticidal-substance containing body for heat-transpiration in which a mixture of a thermoplastic resin powder and an inorganic powder and/or an organic powder is heated to around the melting point of the thermoplastic resin powder, and describe that the heating temperature may be decreased by using a carrier of high heat conductivity. However, it is difficult to obtain the stable transpiration performance over a long period, so that the insecticidal-substance containing body has not been put into practical use.

SUMMARY OF THE INVENTION

An object of the present invention is to provide a long-acting insecticidal mat the insecticidal effect of which may stably be kept for a long period, not less than five days, and to provide a heat-transpiration insecticidal method using the same, which will reverse the conventional findings in the electric mosquito-repellent mat system in which a fibrous mat containing an insecticidal ingredient is set on a radiation plate of a heating element to transpire the insecticidal ingredient.

In order to attain the object described above, the present inventors investigated in details the physicochemical properties of the insecticidal ingredients impregnated in the fibrous mat and the influence of the relationship between the area of the mat and that of the radiation plate upon the transpiration performance, and found that the insecticidal effect could be kept for not less than five days by combining the particular mat with the heat-transpiration apparatus having the particular radiation plate.

That is, a first aspect of the present invention relates to a long-acting insecticidal mat comprising a fibrous mat which is impregnated with not less than 50 mg per mat of an insecticidal ingredient of pyrethroid having not less than $4.0 \times 10^{-6}$ mmHg of vapor pressure at 20° C., wherein the mat is used by means of setting on a radiation plate which has an area of 0.2 to 0.6 time as large as the base area of the mat and has a heating temperature of 70 to 170° C., and is capable of maintaining its insecticidal effect continuously for not less than five days.

The insecticidal ingredient used in the present invention is a pyrethroid compound of high safety which essentially has not less than $4.0 \times 10^{-6}$ mmHg of vapor pressure at 20° C. When the vapor pressure is less than $4.0 \times 10^{-6}$ mmHg, the desired effect can not be obtained even if the heat-transpiration apparatus having the particular radiation plate is combined. Suitable insecticidal ingredients may be exemplified by allethrin, furamethrin, prallethrin, tefuramethrin (5-propargyl-2-furylmethyl 2,2,3,3,-tetramethylcyclopropanecarboxylate), terallethrin, empenthrin, 5-propargyl-2-methyl-3-furylmethyl 2,2,3,3-tetramethylcyclopropanecarboxylate, fenfluthrin and so on, for example, and properly selected according to the use and object thereof. Of those, allethrin, furamethrin, prallethrin and tefuramethrin are preferable in the performance. It should be noted that when they have optical isomers and geometrical isomers attributed to asymmetric carbons and double bonds in the chemical structure, the isomers and optional mixtures of them may naturally be included in the scope of the insecticidal ingredient of the present invention.

In the present invention, the fibrous mat contains not less than 50 mg per mat of the insecticidal ingredient of pyrethroid. When the ingredient is less than 50 mg, the insecticidal effect may naturally not be kept for a long period. Incidentally, when the fibrous mat is impregnated, an undiluted solution added with a stabilizer for the insecticidal ingredient, volatilization controlling agent, solvent, perfume, dye and the like other than the insecticidal ingredient of pyrethroid, is normally used. However, because of limitations of the maximum amount of the solution to be retained, the amount of the undiluted solution is properly controlled, for example, within 1.2 g per mat which is 22×35 mm in size and 2.8 mm in thickness.

The stabilizer for the insecticidal ingredient is exemplified by dibutylhydroxytoluene, dibutylhydroquinone and 2,2'-methylene-bis(4-ethyl-6-t-butylphenol) [Yoshinox 425], and the volatilization controlling agent is exemplified by piperonyl butoxide, N-(2-ethylhexyl)-1-isopropyl-4-methylbicyclo[2.2.2]oct-5-ene-2,3-dicarboxyimide [Synepirine 500], butyl stearate and the like. However, it is naturally not limited thereto.

In addition, in the present invention, the active ingredient other than the insecticidal ingredient of pyrethroid, for example, acaricides, repellents, spatial bactericides and antibacterials such as hinokitiol, linalool, citral, pinene, menthol, terpene alcohols, etc., and fungicides and the like may be added to give a multipurpose composition so long as the transpiration property of the insecticidal ingredient of pyrethroid is not impaired.

The present invention is characterized by combining the particular mat described above with the heat-transpiration apparatus provided with the particular radiation plate which has an area of 0.2 to 0.6 time as large as the base area of the mat and has a heating temperature of 70 to 170° C. The mechanism in which the transpiration of the insecticidal ingredient from the mat is kept constant may be considered as follows. Firstly, when an electric current is applied thereto, the insecticidal ingredient is transpired from the mat part which is set on the radiation plate. However, since the area of the radiation plate is reduced to 0.2 to 0.6 time as large as the base area of the mat, the initial transpiration amount is not so excessively high as in the conventional products. After that, when the electric current is turned off, the insecticidal ingredient in the unheated part of the mat is moved to the mat part on the radiation plate so as to equilibrate the generated concentration gradient of the insecticidal ingredient. In this manner, the desired amount of the insecticidal ingredient is always supplied to the mat part on the radiation plate, and therefore the transpiration amount with the time elapsed in a day is kept almost constant, which is different from the cases in the conventional products. It is also capable of maintaining the transpiration for a long period, not less than five days. It should be noted that although the occupied portion of the radiation plate may be disposed in the middle or edge portion of the mat base, it is preferably in the middle portion of the mat to obtain more stable performance.

A second aspect of the invention as described in the first aspect of the invention is the long-acting insecticidal mat, wherein the mat contains one or two kinds of the compounds selected from allethrin, furamethrin, prallethrin and tefuramethrin especially as the insecticidal ingredient of pyrethroid.

A third aspect of the invention as described in the first or second aspect of the invention is the long-acting insecticidal mat, wherein the mat contains from 150 to 400 mg per mat of furamethrin selected as the insecticidal ingredient of pyrethroid and is added with 50 to 300 mg of piperonyl butoxide as a volatilization controlling agent, and the radiation plate has an area of 0.5 time as large as the base area of the mat.

A fourth aspect of the invention relates to a heat-transpiration insecticidal method using the long-acting insecticidal mat as described in the first aspect of the invention, that is, a fibrous mat which is impregnated with not less than 50 mg per mat of an insecticidal ingredient of pyrethroid having not less than $4.0 \times 10^{-6}$ mmHg of vapor pressure at 20° C. is used by means of setting the mat on a radiation plate which has an area of 0.2 to 0.6 time as large as the base area of the mat and has a heating temperature of 70 to 170° C., and is capable of maintaining the insecticidal effect continuously for not less than five days.

This method is a heat-transpiration insecticidal method of extremely high practicality, since it follows the advantage of the electric mosquito-repellent mat that is clean, it is free from a fear of leakage of the liquid, which is different from the case in the liquid mosquito-repellent, and it is capable of maintaining the insecticidal effect for a long period.

A fifth aspect of the invention as described in the fourth aspect of the invention is a heat-transpiration insecticidal method, wherein the mat contains one or two kinds of the compounds selected from allethrin, furamethrin, prallethrin and tefuramethrin especially as the insecticidal ingredient of pyrethroid.

A sixth aspect of the invention is the method as described in the fourth aspect or the fifth aspect of the invnention, wherein the mat contains from 150 to 400 mg per mat of furamethrin selected as the insecticidal ingredient of pyrethroids and is added with 50 to 300 mg of piperonyl butoxide as a volatilization controlling agent, and the radiation plate has an area of 0.5 time as large as the base area of the mat.

DESCRIPTION OF THE INVENTION

According to the structure as described in the first aspect of the invention, there is provided a long-acting insecticidal mat which is capable of maintaining the insecticidal effect continuously for not less than five days by combining the physicochemical properties of the insecticidal ingredient impregnated in the fibrous mat with the relationship between the area of the mat and that of the radiation plate.

As the material for the fibrous mat, that of the same quality as the conventional products such as pulp, linter, or a mixture of them may be used. The size and shape are also optional, but the one according to the conventional standards can be used with ease. The mat is impregnated with not less than 50 mg per mat of an insecticidal ingredient of pyrethroid having not less than $4.0 \times 10^{-6}$ mmHg of vapor pressure at 20° C. However, the undiluted solution is suitably prepared by adding a stabilizer and volatilization controlling agent suitable for the insecticidal ingredient, solvent, perfume, dye and the like in consideration of the manufacturing process, use and object.

In addition, with respect to the radiation plate which has an area of 0.2 to 0.6 time as large as the base area of the mat described above and has a heating temperature of 70 to 170° C., the position in the heat-transpiration apparatus, the shape and the like may be optionally decided. For instance, the radiation plate in the round shape of approximately 14 to 18 mm in diameter or that in the shape of the belt approximately 8 to 18 mm in width may be provided in the middle portion and the support that supports the peripheral portion of the mat may be arranged. Or, instead of the support, a proper setting plate may be combined so as to have a space between the radiation plate described above.

According to the structure of the second aspect of the invention, there is provided a long-acting insecticidal mat having more excellent performance, since one or two kinds of compounds especially selected from allethrin, furamethrin, prallethrin and tefuramethrin as the insecticidal ingredient of pyrethroid are used.

According to the structure of the third aspect of the invention, there is provided a long-acting insecticidal mat having still further excellent performance, since furamethrin which gives the optimal performance as the insecticidal ingredient of pyrethroid, the content thereof, and the volatilization controlling agent are selected, and further the efficient proportion of the area of the radiation plate to that of the mat is specified.

According to the structure of the fourth aspect of the invention, there is provided a heat-transpiration insecticidal method having extremely high practicality that follows the advantage of the electric mosquito-repellent mat which is clean, which is free from a fear of leakage of the liquid, which is different from the case in the liquid mosquito-repellent, and which is capable of maintaining the insecticidal effect for a long period by using the long-acting insecticidal mat of the first aspect of the invention.

According to the structure of the fifth aspect of the invention, there is provided a more useful heat-transpiration insecticidal method, since one or two kinds of compounds especially selected from allethrin, furamethrin, prallethrin and tefuramethrin as the insecticidal ingredient of pyrethroid are used.

According to the structure of the sixth aspect of the invention, there is provided a still further useful heat-transpiration insecticidal method, since furamethrin which gives the optimal performance as the insecticidal ingredient of pyrethroid, the content thereof, and the volatilization controlling agent are selected, and further the efficient proportion of the area of the radiation plate to that of the mat is specified.

DETAILED DESCRIPTION OF THE PREFERRED EMBODIMENTS

The present invention will be further described with reference to the following examples and examination example.

Example 1

The fibrous mat 22×35 mm in size and 2.8 mm in thickness was impregnated with an undiluted mat solution containing 300 mg of d-trans-allethrin (trade name: Esbiothrin), 200 mg of piperonyl butoxide as a volatilization controlling agent, 10 mg of a stabilizer, and a slight amount of perfume and a blue dye. When the mat was used by means of setting on a heat-transpiration apparatus having a round radiation plate of 16 mm in diameter and having a radiation temperature of 150° C. in the middle portion of the apparatus, and the supports that support the mat were arranged at four peripheral portions of the radiation plate, the transpiration amount of d-trans-allethrin for 12 hours per day was approximately 30 mg. This mat exhibited the stable transpiration performance and insecticidal effect for 10 days. Further, there was no fear of leakage of the liquid etc., and was excellent in use.

Example 2

The fibrous mat 22×35 mm in size and 2.8 mm in thickness was impregnated with the kerosene solution containing 250 mg of d-cis,trans-furamethrin (trade name: Pynamin D-f), 150 mg of piperonyl butoxide as a volatilization controlling agent, 20 mg of a stabilizer, and a slight amount of a blue dye. The heat-transpiration apparatus having a radiation plate in a shape of the belt which had an area of 0.5 time as large as the base area of the mat was arranged in the middle portion of the apparatus, and an electric current was applied for 12 hours in the nighttime and turned off in the daytime and this cycle was repeated for 10 days. As a result, the transpiration amount of d-cis,trans-furamethrin per day was approximately 20 mg and stable with the time elapsed, and the adequate insecticidal effect was exhibited over 10 days.

Test Example 1

The insecticidal mat shown in table 1 was prepared in accordance with Examples 1 and 2 to set on the various heat-transpiration apparatuses, and a variety of performance was examined.

(1) Transpiration Performance

The transpired insecticidal ingredient was trapped with silica gel-packed column in every preset time, and the insecticidal ingredient was extracted with acetone, and then analyzed by gas chromatography to obtain the transpiration amount per hour. The values given in table 1 are shown as the relative ratios based on the initial values of the respective products defined as 1.00.

(2) Insecticidal Effect

The knock-down effect on *Culex pipiens* was evaluated in every preset time by the open cylinder method described below. The values given in table 1 are shown as the relative significant ratios based on the initial values of the one-day mat containing 40 mg of dl,d-cis,trans-allethrin defined as 1.00.

Open Cylinder Method

Two plastic cylinders of 20 cm in inside diameter and 43 cm in height are piled up. A cylinder of 20 cm both in inside diameter and height is partitioned vertically with a wire net of 16 mesh (the place where the mosquitos tested are put in), and is placed thereon. A cylinder of 20 cm in inside diameter and height is further placed thereon. This set consisting of the four cylinders is placed on a stand, and the heat-transpiration apparatus is placed in the middle of the stand to transpire the insecticidal ingredient in the mat to be examined. Then, about 20 mosquitos to be tested are released in the upper stair of the cylinder set and the number of mosquitos knocked down is observed with the time elapsed. After 20 minutes exposure, all the mosquitos tested are moved to a sanitary polyethylene container and 30% sugar water was fed to the mosquitos, and the insecticidal rate is determined after 24 hours keeping.

TABLE 1

| | Mat Containing Ingredient (mg/mat) | | Radiation Plate | | Transpiration Performance | | | Insecticidal Effect | | |
|---|---|---|---|---|---|---|---|---|---|---|
| | Insecticidal Ingredient (vapor pressure: mmHg/20° C.) | Other Ingredient | Size (area ratio to mat) | Temperature ° C. | Initial | 2 Days after | 5 Days after | Initial | 2 Days after | 5 Days after |
| Present Invention | | | | | | | | | | |
| 1 | Esbiothrin 300 ($4.2 \times 10^{-5}$) | piperonyl butoxide 200 | φ16 mm (0.26) *peripheral support | 150 | 1.00 | 0.94 | 0.88 | 1.26 | 1.20 | 1.15 |

TABLE 1-continued

|  | Mat Containing Ingredient (mg/mat) | | Radiation Plate | | Transpiration Performance | | | Insecticidal Effect | | |
|---|---|---|---|---|---|---|---|---|---|---|
|  | Insecticidal Ingredient (vapor pressure: mmHg/20° C.) | Other Ingredient | Size (area ratio to mat) | Temperature ° C. | Initial | 2 Days after | 5 Days after | Initial | 2 Days after | 5 Days after |
| 2 | d-cis,trans-furamethrin 250 ($1.3 \times 10^{-4}$) | piperonyl butoxide 150 | Belt 17 × 22 mm in the middle (0.49) | 120 | 1.00 | 0.95 | 0.90 | 1.50 | 1.41 | 1.34 |
| 3 | prallethrin 80 ($3.5 \times 10^{-5}$) | isopropyl myristate 100 | Belt 12 × 22 mm in the middle (0.34) | 165 | 1.00 | 0.92 | 0.85 | 1.23 | 1.17 | 1.12 |
| 4 | empenthrin 300 ($6.5 \times 10^{-4}$) | silicon oil 200 | φ14 mm (0.20) *peripheral support | 80 | 1.00 | 0.93 | 0.86 | 1.19 | 1.10 | 1.03 |
| 5 | dl,d-cis,trans-allethrin 400 ($4.2 \times 10^{-5}$) | piperonyl butoxide 200 | Belt 17 × 22 mm on the half side (0.49) | 160 | 1.00 | 0.93 | 0.88 | 1.21 | 1.16 | 1.12 |
| 6 | transfluthrin 250 ($4.0 \times 10^{-6}$) | Synepirine-500 100 | φ16 mm (0.26) *peripheral setting plate | 100 | 1.00 | 0.96 | 0.90 | 1.32 | 1.23 | 1.18 |
| 7 | terallethrin 300 ($2.2 \times 10^{-4}$) | butyl stearate 150 | Belt 21 × 22 mm in the middle (0.60) | 130 | 1.00 | 0.94 | 0.86 | 1.24 | 1.17 | 1.10 |
| Comparison | | | | | | | | | | |
| 1 | d-cis,trans-phenothrin 200 ($1.4 \times 10^{-7}$) | piperonyl butoxide 50 | φ16 mm (0.26) *peripheral support | 170 | 1.00 | 0.64 | 0.47 | 0.30 | 0.24 | 0.13 |
| 2 | Esbiothrin 40 ($4.2 \times 10^{-5}$) | piperonyl butoxide 100 | φ16 mm (0.26) *peripheral support | 145 | 1.00 | 0.23 | — | 1.29 | 0.21 | — |
| 3 | Esbiothrin 300 ($4.2 \times 10^{-5}$) | Synepirine-500 200 | 25 × 37 mm (1.00) *conventional radiation plate | 140 | 1.00 | 0.57 | 0.04 | 1.36 | 0.63 | — |
| 4 | Esbiothrin 300 ($4.2 \times 10^{-5}$) | piperonyl butoxide 200 | φ7 mm (0.05) *peripheral support | 125 | 1.00 | 0.86 | 0.78 | 0.74 | 0.65 | 0.59 |
| 5 | Esbiothrin 300 ($4.2 \times 10^{-5}$) (inorganic powder solid product) | — | 25 × 37 mm (1.00) *conventional radiation plate | 170 | 1.00 | 0.80 | 0.63 | 1.05 | 0.82 | 0.56 |

As a result, the present invention comprising a combination of the particular mat with the heat-transpiration apparatus having the particular radiation plate exhibited an excellent transpiration performance and an insecticidal effect for not less than five days, which is convenient and extremely practical in use. On the contrary, in any cases in which the insecticidal ingredient of pyrethroid having less than $4.0 \times 10^{-6}$ mmHg of vapor pressure at 20° C. was used (Comparative example 1), in which less than 50 mg of the insecticidal ingredient per mat having not less than $4.0 \times 10^{-6}$ mmHg of vapor pressure was used (comparative example 2), in which the conditions of the radiation plate were not suitable (Comparative examples 3 and 4), and in which the insecticidal substance container disclosed in Japan Patent Application Laid-open No. Hei 5-194103 was used (Comparative example 5), the satisfactory performance was not obtained.

According to the invention of any one of the first to third aspects of the present invention, a long-acting insecticidal mat which is a clean product and free from a fear of leakage of the liquid, and which is capable of maintaining the insecticidal effect for a long period, not less than five days, is provided.

According to the invention of any one of the fourth to sixth aspects of the present invention, a heat-transpiration insecticidal method which is extremely practical in use and is effective for a long period in the electric mosquito-repellent mat system is provided by combining the long-acting insecticidal mat of the first to third aspects of the present invention with the heat-transpiration apparatus having the particular radiation plate.

What is claimed is:
1. A heat-transpiration insecticidal method, comprising:
impregnating a fibrous mat with at least one insecticidal ingredient of pyrethroid selected from the group consisting of allethrin, furamethrin, prallethrin, tefuramethrin, terallethrin, empenthrin, 5-propargyl-2-methyl-3-furyimethyl 2,2,3,3-tetramethylcyclopropanecarboxylate and fenfluthrin, and as a volatilization controlling agent piperonyl butoxide, in a weight ratio of said insecticidal ingredient of pyrethroid to said volatilization controlling agent equals 3 or less, and with not less than 50 mg per mat of said insecticidal ingredient of pyrethroids;
setting the mat on a radiation plate which has an area of 0.2 to 0.6 time as large as the base area of the mat and has a heating temperature of 70 to 170° C.; and
maintaining the insecticidal effect continuously for not less than five days.
2. The heat-transpiration insecticidal method as claimed in claim 1, wherein the insecticidal ingredient of pyrethroid is one or two compounds selected from the group consisting of allethrin, furamethrin, prallethrin and tefuramethrin.

3. The heat-transpiration insecticidal method as claimed in claim 1, wherein the mat contains from 150 to 400 mg per mat of furamethrin as the insecticidal ingredient of pyrethroid and 50 to 300 mg of piperonyl butoxide as a volatilization controlling agent, and the radiation plate has an area of 0.5 time as large as the base area of the mat.

* * * * *